US005922775A

United States Patent [19]
Kun et al.

[11] Patent Number: 5,922,775
[45] Date of Patent: Jul. 13, 1999

[54] METHOD OF TREATING MALIGNANT TUMORS WITH KETONE THYROXINE ANALOGUES HAVING NO SIGNIFICANT HORMONAL ACTIVITY

[75] Inventors: Ernestt Kun, Mill Valley; Jerome Mendeleyev, Tiburon; Kalman G. Buki, San Francisco, all of Calif.

[73] Assignee: Octamer, Inc., Berkeley, Calif.

[21] Appl. No.: 08/956,711

[22] Filed: Oct. 23, 1997

[51] Int. Cl.[6] .................................................. A61K 31/12
[52] U.S. Cl. ............................................................. 514/685
[58] Field of Search ............................................ 514/685

[56] References Cited

U.S. PATENT DOCUMENTS

| 4,724,234 | 2/1988 | Cone, Jr. ................................. 514/728 |
| 4,816,255 | 3/1989 | Ghent et al. ............................. 424/150 |
| 5,736,576 | 4/1998 | Kun et al. ................................ 514/570 |

FOREIGN PATENT DOCUMENTS

| 642159 | 8/1950 | United Kingdom . |
| 643089 | 9/1950 | United Kingdom . |
| WO 93/2444 A1 | 12/1993 | WIPO . |

OTHER PUBLICATIONS

Borrows et al., "The Synthesis of Thyroxine and Related Substances. Part I. The Preparation of Tyrosine and Some of its Derivatives, and a New Route to Thyroxine," *J. Chem. Soc.* 1949 (Supp. Issue No. 1):S185–S190 (1949).

Borrows et al., "The Synthesis of Thyroxine and Related Substances. Part II. Preparation of Dinitrophenyl Ethers," *J. Chem. Soc.* 1949 (Supp. Issue No. 1):S190–S199 (1949).

Borrows et al., "Diphenyl Ethers," *Chem. Abstr.* 44:574h (1950).

Borrows et al., "Synthesis of Thyroxine and Related Substances. I. The Preparation of Tyrosine and Some of its Derivatives and a New Route to Thyroxine," *Chem. Abstr.* 45:P7594b (1951).

Burton et al., "Traction Forces of Cytokinesis Measured With Optically Modified Elastic Substrate," *Nature* 385:450–454 (1997).

Cason "The Use of Organocadmium Reagents for the Preparation of Ketones", *Chem. Rev.* 40:15–32 (1947).

Clayton et al., "The Synthesis of Thyroxine and Related Substances. Part VIII. The Preparation of Some Halogeno– and Nitro–diphenyl Ethers," *J. Am. Chem. Soc.* 1951:2467–2473 (1951).

Clayton et al., "Synthesis of Thyroxine and Related Substances. VIII. The Preparation of Some Halo–and Nitrodiphenyl Ethers," *Chem. Abstr.* 46:8056g (1952).

Cookson et al., "The Synthesis of Thyroxine and Related Substances. Part IX. Analogues of Thyroxine with Modified Side Chains," *J. Chem. Soc.* 827–833 (1952).

Crowder et al., "Bisbenzylisoquinolines. II. Synthesis of 5–2(2–Amino–Ethyl)–4'–Carboxy–2,3–Dimethoxydiphenyl Ether," *Chem. Abstr.* 52:17163d (1958).

Crowder et al., "Bisbenzylisoquinolines. Part II. The Synthesis of 5–(2–Aminoethyl)–4'–carboxy–2,3–dimethoxydiphenyl Ether," *J. Chem. Soc.* 1958:2142–2149 (1958).

Dibbo et al., "The Synthesis of Thyroxine and Related Compounds. Part XVII.[1] The Preparation of Some Additional Compounds Related to Thyroxine," *J. Chem. Soc.* 2890–2902 (1961).

Dunphy, "The Decision to Enter Mitosis," *Trends Cell. Biol.* 4:202–207 (1994).

Dykes et al., "Response of Human Tumor Xenographs in Athymic Nude Mice to Docetaxel," *Biosis* 95:487870 (1995).

Gemmill et al., "3–Iodo–, 3,3'–Diiodo–and 3,3'–Diiodo–5–broythyroxine," *J. Am. Chem. Soc.* 78:2434–2436 (1956).

Grinberg et al., "Studies with Mouse Pituitary Thyrotropic Tumors. V. Effect of Varous Thyroxine Analogs on Growth and Secretion," *Chem. Abstr.* 57:14335d (1962).

Grinberg et al., "Studies with Mouse Pituitary Thyrotropic Tumors. v. Effect of Various Thyroxine Analogs on Growth and Secretion," *Cancer Research* 22:835–841 (1962).

Grutzmeier, S., "Myxoedema in a Case of Acute Myoloid Leukemia," *EMBASE* 85:118288 (1985).

Jorgensen, "Thyroid Hormones and Analogues. I. Synthesis, Physical Properties and Theoretical Calculations," In: *Hormonal Proteins and Peptides* VI:57–105, C.H. Li, Ed., Academic Press, NY (1978).

Jorgensen, "Thryoid Hormones and Analogues II. Structure– Activity Relationships," In: *Hormonal Proteins and Peptides*, C.H. Li, Ed. Academic Press, N VI:107–204, Y (1978).

Kawabe et al., "HOXII Interacts with Protein Phosphatase PP2A and PP1 and Disrupts G2/M Cell Cycle Checkpoint," *Nature* 385:454–458 (1997).

Kumaoka et al., "The Effect of Thyroxine Analogs on a Transplantable–Mouse Pituitary Tumor," *Chem. Abstr.* 54:18779i (1960).

Kumaoka et al., "The Effect of Thyroxine Analogues on a Transplantable Mouse Pituitary Tumor," *Endocrinology* 66:32–38 (1960).

Kun et al., "Induction of Tumor Apotosis by Methyl–3., 5–Diiodo–4–4(4'–Methoxyphenoxy) Benzoate (DIME)," Abstract No. 102, *Int. J. Oncol.* 9:supplement 829 (1996).

Kun et al., "Method of Treating Malignant Tumors with Thyroxine analogues Having no Significant Hormonal Activity," U.S. Patent Application Serial No 08/833,272 – filed Apr. 3, 1997.

(List continued on next page.)

*Primary Examiner*—Jerome D. Goldberg
*Attorney, Agent, or Firm*—Albert P. Halluin; Howrey & Simon

[57] ABSTRACT

The present invention provides methods for treating cancer, particularly malignant tumors, with ketone thyroxine analogues having no significant hormonal activity. A ketone thyroxine analogue is administered to an afflicted mammal in an amount effective to cause depression or regression of malignant tumor growth or to treat cancer. Particularly preferred ketone thyroxine analogues are those capable of causing about 35 percent or more inhibition of initial velocity of microtubule protein assembly in vitro.

7 Claims, 3 Drawing Sheets

OTHER PUBLICATIONS

Masuda et al., "Thyroxine Related Compounds. I. Synthesis of Triidothyroformic Acid and its Derivatives," *Takeda Kenkyusho Ho* 29(4);545–552 (in Japanese) (1970).

Masuda et al., "Triidothyroformic Acid," *Chem. Abstr.* 75:140431 q (1971).

Meltzer et al., "Thyroxine Analogs," *J. Org. Chem.* 22:1577–1581 (1957).

Meltzer et al., "Thyroxine Analogs," *Chem. Abstr.* 52:7210d (1958).

Mendeleyev et al., "Structural Specificity and Tumoricidal Action of Methyl–3,5–Diiodo–4–(4'–Methoxyphenoxy) Benzoate (DIME)," *Intl. J. Oncol.* 10:689–695 (1997).

Money et al., "The Effect of change in Chemical Structure of Some Thyroxine Analogues on the Metamorphosis of Rana Pipiens Tadpoles,"0 *Endocrinology* 63:20–28 (1958).

Money et al., "The Effect of Various Thyroxine Analogues on Suppression of Iodine–131 Uptake by the Rat Thyroid," *Endocrinology* 64:123–125 (1959).

Money et al., "The Effect of Change in Chemical Structure of Some thyroxine Analogs on the Metamorphosis of Rana Pipiens Tadpoles," *Chem. Abstr.* 52:20701a (1958).

Money et al., "Effect of Various Throxine Analogs on Suppressionof Iodine–131 Uptake by the Rat Thyroid," *Chem. Abstr.* 53:14327i (1959).

Stasilli et al., "Antigoitrogenic and Calorigenic Activities of Thyroxine Analogues in Rats," *Endocrinology* 64:62–82 (1959).

Stasilli et al., "Analogs in Rats," *Chem. Abstr.* 53:14327ci (1959).,

Tiwari et al., "A pH and Temperature–Dependent Cycling Method that Doubles the Yield of Microtubule Protein," *Anal Biochem.* 215:96–103 (1993).

Tomita et al., "Synthesis and Biological Activity of Some Triiodinated Analogues of Thyroxine," *J. Biol. Chem.* 219:595–604 (1956).

Wera et al., "Serine/Threonine Protein Phosphatases," *Biochem. J.* 311:17–29 (1995).

METHOD OF TREATING MALIGNANT TUMORS WITH KETONE THYROXINE ANALOGUES HAVING NO SIGNIFICANT HORMONAL ACTIVITY

FIELD OF THE INVENTION

The present invention relates generally to the field of cancer therapeutics. More specifically, the present invention relates to the use of ketone thyroxine analogues having no significant hormonal activity, particularly 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP), as potent, selective and non-toxic anti-tumor agents.

BACKGROUND OF THE INVENTION

Malignant cancerous growths, due to their unique characteristics, pose serious challenges for modern medicine. These characteristics include uncontrollable cell proliferation resulting in unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation.

Antineoplastic chemotherapy currently encompasses several groups of drugs including alkylating agents, purine antagonists and antitumor antibiotics. Alkylating agents alkylate cell proteins and nucleic acids preventing cell replication, disrupting cellular metabolism and eventually leading to cell death. Typical alkylating agents are nitrogen mustard, cyclophosphamide and chlorambucil. Toxicities associated with alkylating agents treatment include nausea, vomiting, alopecia, hemorrhagic cystitis, pulmonary fibrosis and an increased risk of developing acute leukemia.

Purine, pyrimidine and folate antagonists are cell cycle and phase specific and, in order to promote an anti-tumor effect, they require cells to be in the cell replication cycle and in the DNA synthesis phase of replication. The purine antagonists such as 6-mercaptopurine or 6-thioguanidine inhibit de novo purine synthesis and interconversion of purines. The pyrimidine antagonists, such as cytarabine, 5-fluorouracil or floxuridine, inhibit DNA synthesis by inhibiting deoxycytidylate kinase and DNA polymerase.

Folate antagonists, e.g., methotrexates, bind tightly with the intracellular enzyme dihydrofolate reductase ultimately leading to cell death resulting from an inability to synthesize pyrimidines. Toxicities associated with the use of these compounds include alopecia, myelosuppression, vomiting, nausea, and cerebellar ataxia, among others.

Plant alkaloids such as vincristine, vinblastine or podophyllotoxins etoposide and teniposide generally inhibit mitosis and DNA synthesis and RNA dependent protein synthesis. Toxicities of these drugs are similar to those described above and include myopathy, myelosuppression, peripheral neuropathy, vomiting, nausea and alopecia.

Antitumor antibiotics such as doxorubicin, daunorubicin and actinomycin act as intercalators of DNA, preventing cell replication, inhibiting synthesis of DNA-dependent RNA and inhibiting DNA polymerase. Bleomycin causes scission of DNA and mitomycin acts as inhibitor of DNA synthesis by bifunctional alkylation. Toxicities of these antibiotics are numerous and severe and include necrosis, myelosuppression, anaphylactic reactions, anorexia, dose-dependent cardiotoxicity and pulmonary fibrosis.

Other compounds used for chemotherapeutical treatment of cancer are inorganic ions such as cisplatin, biologic response modifiers such as interferon, enzymes and hormones. All these compounds, similarly to those mentioned above, are accompanied by toxic adverse reactions.

Accordingly, it would be extremely advantageous to provide safe and non-toxic chemotherapeutic compositions which would effectively inhibit and/or suppress tumor cell proliferation and/or neoplastic growth. Furthermore, it would be extremely advantageous to provide safe, effective and non-toxic chemotherapeutic compositions that are easy to administer.

The identification of safe, effective, non-toxic, and orally administrable organic compounds capable of depressing or regressing malignant tumor growth in mammals and the use of such compounds to treat cancer is therefore desirable and the object of this invention.

SUMMARY OF THE INVENTION

The present invention relates to the use of certain ketones which are thyroxine analogues and which have no significant hormonal activity, particularly 1-[3,5-diiodo-4-(4'-methoxyphenoxy)-phenyl]-ethanone ("DIPE") and 1-[3,5-diiodo-4-[4'-methoxyphenoxy)-phenyl]-1-propanone ("DIPP") to depress or regress malignant tumor growth and to treat cancer. The method generally involves administering to a mammal an amount of one or more of the certain ketones which are thyroxine analogues in an amount effective to depress or regress malignant tumor growth or to treat cancer. The compounds of the present invention typically are characterized as lacking significant hormonal activity.

In particular, the present invention relates to a method for treating a malignant tumor in a mammal, the method comprising administering to a mammal having a malignant tumor an amount of a ketone which is a thyroxine analogue sufficient to depress growth of the malignant tumor, wherein the ketone is characterized as being a compound capable of causing about 35 percent or more inhibition of initial velocity of microtubule protein assembly in vitro, preferably about 45 percent or more, more preferably about 70 percent or more, and most preferably about 90 percent or more inhibition of microtubule protein assembly in vitro.

In one illustrative embodiment, compounds useful in the methods of the present invention have the structural formula:

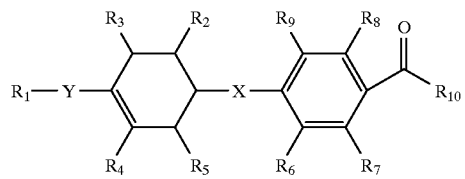

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxy, $(C_1-C_4)$ alkoxy and halogen;

$R_6$, $R_7$, $R_8$ and $R_9$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy, halogen, $NO_2$ and $NH_2$; and $R_{10}$ is selected from the group consisting of ($C_1$–$C_4$) alkyl, ($C_1$–$C_4$) alkenyl, and ($C_1$–$C_4$) alkynyl.

In another illustrative embodiment, compounds useful in the methods of the present invention have the structural formula:

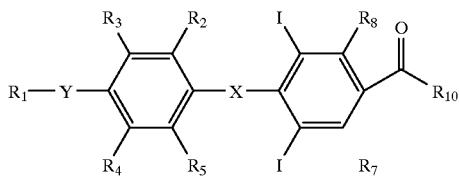

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy and halogen;

$R_7$ and $R_8$ are each independently selected from the group consisting of: H, ($C_1$–$C_4$) alkyl, ($C_1$–$C_4$) alkenyl, ($C_1$–$C_4$) alkynyl, hydroxy, ($C_1$–$C_4$) alkoxy halogen, $NO_2$ and $NH_2$; and $R_{10}$ is selected from the group consisting of ($C_1$–$C_4$) alkyl, ($C_1$–$C_4$) alkenyl, and ($C_1$–$C_4$) alkynyl.

In a preferred embodiment of the invention, the ketone is one of 1-[3,5-diiodo-4-(4'-methoxyphenoxy)-phenyl]-ethanone (DIPE) or 1-[3,5-diiodo-4-(4'-methoxyphenoxy)-phenyl]-ethanone (DIPE) or 1-[3,5-diiodo-4-(4'-methoxyphenpxy-1-propanone (DIPP).

DETAILED DESCRIPTION OF THE INVENTION

Definitions

As used herein

Figure 1:
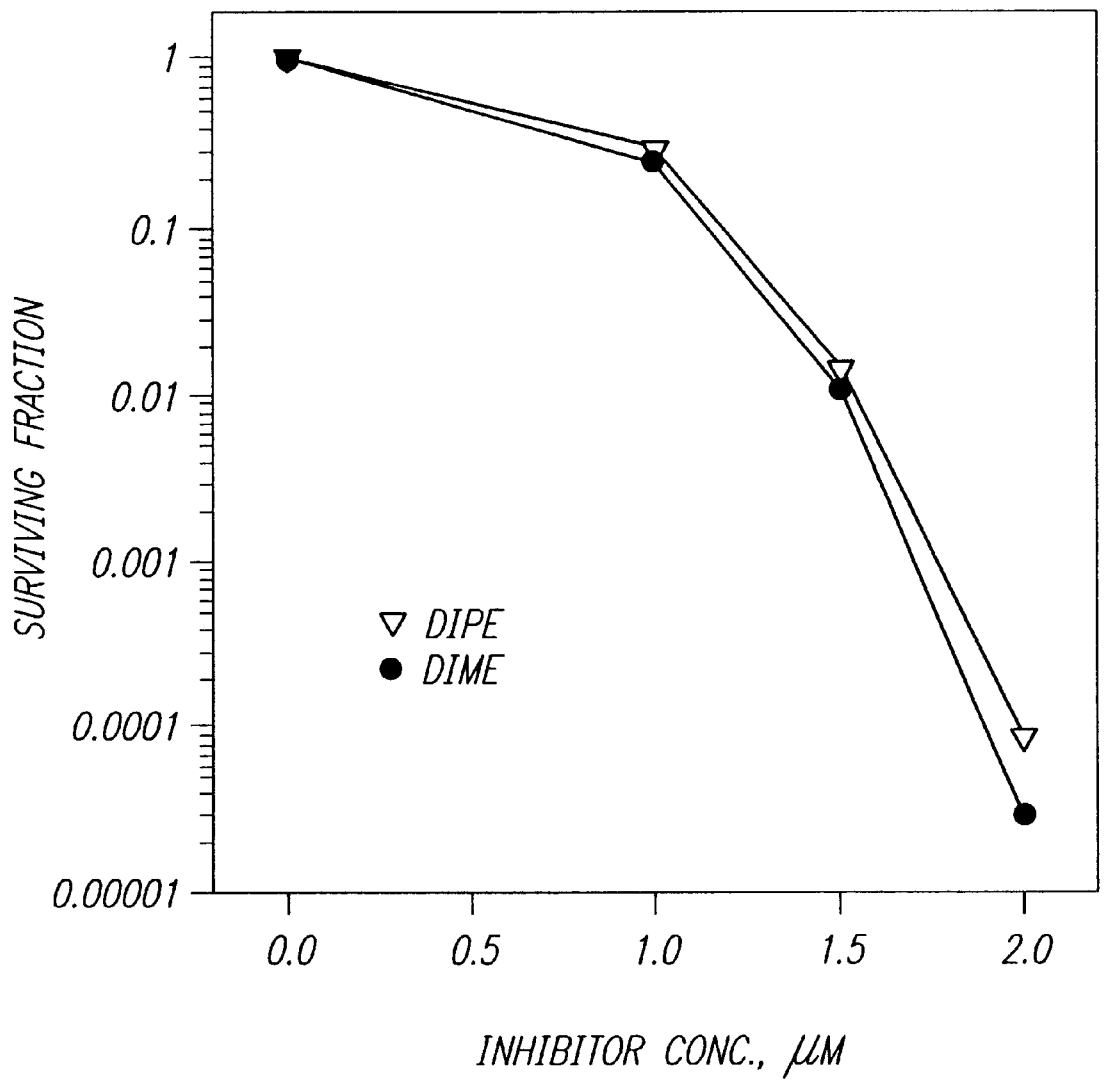
FIG. 1 is a graph illustrating the cell killing effects of DIME and DIPE on mammary cancer colonies.

"Alkyl" refers to a saturated branched, straight chain or cyclic hydrocarbon radical. Typical alkyl groups include methyl, ethyl, propyl, isopropyl, cyclopropyl, butyl, isobutyl, cyclobutyl, tert-butyl, pentyl, hexyl and the like.

"Alkenyl" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

"Alkynyl" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

"Mammal" refers to animals or humans.

"Pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts include, for example, alkali metal salts such as sodium and potassium, alkaline earth salts and ammonium salts.

"Pharmacophore" refers to the critical three-dimensional arrangement of molecular moieties or fragments (or the distribution of electron density) that is recognized by a receptor (Burger's Medicinal Chemistry and Drug Delivery Vol. I: Principles and Practice 619, 5th Edition, John Wiley & Sons, New York).

"Therapeutically effective amount" refers to an amount of a compound or composition effective to depress, suppress or regress malignant cell growth or result in amelioration of symptoms associated with cancerous diseases.

DESCRIPTION OF SPECIFIC EMBODIMENTS

The present invention relates to methods of treating malignant tumors and cancer in mammals with ketones which are analogues of thyroxine and are characterized as having no significant hormonal activity. The present invention is based on the surprising discovery that certain ketone analogues of thyroxine which do not exhibit hormonal activity, and which are resistant to in vivo or cellular esterases and amidases are particularly potent, selective and non-toxic inhibitors of malignant tumor growth. The preferred compounds referred to herein are DIPE and DIPP.

Thyroxine, an amino acid of the thyroid gland (Merck Index, 1989, 9348:1483) and thyroxine analogues are well-known in the art. It is well established in the literature that thyroid hormones, specifically thyroxines T3 and T4, have two distinct types of biological actions: one on cell metabolism, the second on cell differentiation and development (Jorgensen, 1978, "Thyroid Hormones and Analogues II. Structure-Activity Relationships," In: Hormonal Proteins and Peptides, Vol. VI, pp. 107–204, C. H. Li, ed., Academic Press, New York). For example, thyroxine suppresses uptake of iodine by the thyroid (Money et al., 1959, "The Effect of Various Thyroxine Analogues on Suppression of Iocline-131 Uptake by the Rat Thyroid," Endocrinology 64:123–125) and induces cell differentiation as studied by tadpole metamorphosis (Money et al., 1958, "The Effect of Change in Chemical Structure of Some Thyroxine Analogues on the Metamorphosis of Rana Pipiens Tadpoles," Endocrinology 63:20–28). Additionally, thyroxine and certain thyroxine analogues depress growth of non-malignant mouse pituitary thyrotropic tumors (Kumaoka et al., 1960, "The Effect of Thyroxine Analogues on a Transplantable Mouse Pituitary Tumor," Endocrinology 66:32–38; Grinberg et al., 1962, "Studies with Mouse Pituitary Thyrotropic Tumors. V. Effect of Various Thyroxine Analogs on Growth and Secretion," Cancer Research 22:835–841).

The structural requirements of thyroxine and thyroxine analogues for metabolic stimulation and induction of cell differentiation are not identical (see Jorgensen, 1978, "Thyroid Hormones and Analogues II. Structure-Activity Relationships," In: *Hormonal Proteins and Peptides*, Vol. VI, p. 150, C. H. Li, ed., Academic Press, New York). For example, Money et al. have found that there is no correlation between suppression of thyroid iodine uptake and induction of tadpole metamorphosis (Money et al., 1958, "The Effect of Change in Chemical Structure of Some Thyroxine Analogues on the Metamorphosis of Rana Pipiens Tadpoles," *Endocrinology* 63:20–28). Based on these observations, it was conceived that as yet unidentified cellular responses may be altered or induced by certain thyroxine analogues which do not exhibit either mode of action (metabolic or differentiating) exhibited by thyroxine T3 and T4.

The Compounds

Ketone thyroxine analogues useful in the methods of the present invention are generally compounds having the structural formula:

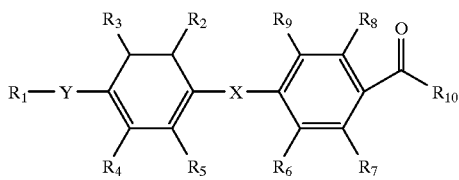

and pharmaceutically acceptable salts thereof, wherein:

$X=O$, S, $CH_2$, carboxy or absent;

$Y=O$ or S;

$R_1$=methyl or ethyl;

$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy and halogen;

$R_6$, $R_7$, $R_8$ and $R_9$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$; and $R_{10}$ is selected from the group consisting of $(C_1-C_4)$ alkyl, $(C_1-C_4)$ alkenyl, and $(C_1-C_4)$ alkynyl.

In a preferred embodiment, compounds useful in the methods of the present invention are compounds having the structural formula:

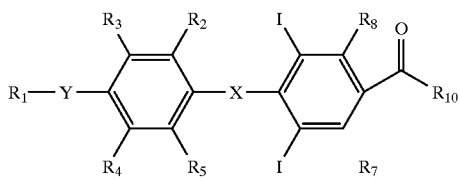

and pharmaceutically acceptable salts thereof, wherein:

$X=O$, S, $CH_2$, carboxy or absent;

$Y=O$ or S;

$R_1$=methyl or ethyl;

$R_2$, $R_3$, $R_4$ and $R_5$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy and halogen;

$R_7$ and $R_8$ are each independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$; and $R_{10}$ is selected from the group consisting of $(C_1$ to $C_4)$ alkyl, $(C_1$ to $C_4)$ alkenyl and $(C_1$ to $C_4)$ alkynyl.

In a particularly preferred embodiment, the compound is selected from the group consisting of 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP).

Thyroxine analogues such as methyl-3,5-diiodo-4-(4'-methoxyphenoxy)benzoate (DIME) have been described in the literature. However, unlike thyroxine, DIME was reported to have no significant metabolic or cell differentiating activity (as determined by tadpole metamorphosis) (Money et al., 1958, "The Effect of Change in Chemical Structure of Some Thyroxine Analogues on the Metamorphosis of Rana Pipiens Tadpoles," *Endocrinology* 63:20–28; Stasilli et al, 1959, "Antigoitrogenic and Calorigenic Activities of Thyroxine Analogues in Rats," *Endocrinology* 64:62–82). For example, uptake of iodine into the thyroid of rats is only marginally (15%) inhibited by DIME as compared to thyroxine (Money et al, 1959, "The Effect of Various Thyroxine Analogues on Suppression of Iodine-131 Uptake by the Rat Thyroid," *Endocrinology* 64:123–125). Furthermore, DIME was reported to have no inhibitory activity against the growth of a non-malignant mouse pituitary adenoma (Kumaoka et al., 1960, "The Effect of Thyroxine Analogues on a Transplantable Mouse Pituitary Tumor," *Endocrinology* 66:32–38; Grinberg et al., 1962, "Studies with Mouse Pituitary Thyrotropic Tumors. V. Effect of Various Thyroxine Analogs on Growth and Secretion," *Cancer Research* 22:835–841). No studies with malignant cells have been reported.

It was previously described in U.S. Ser. No. 08/655,267 filed Jun. 4, 1996 and herein incorporated by reference that certain thyroxine analogues having no significant hormonal activity, particularly DIME, not only inhibit the growth of a variety of malignant cell types, but induce tumor cell apoptosis preceded by micronucleation as well. These cytostatic and cytocidal activities were shown to be sensitive to structure. Testing of thirteen structural analogues and homologues of DIME indicated that even minor alterations of the methyl ester and 4'-methoxy substituents rendered the molecule completely inactive. Whereas DIME was shown to be highly active both in cellular assays and in vivo, the 4'-propoxy and ethyl ester homologues are completely inactive. Accordingly, DIME was shown to define a critical arrangement of molecular moieties, or a pharmacophore, having specific cytostatic and cytocidal activity, and consequently significant chemotherapeutic potential.

Progression of eukaryotic cells through the cell division cycle is primarily controlled by the activity of cyclin-dependent protein kinases. The best studied event is the transition from G2 to M phase, which is controlled by cdc2 kinase complexed with cyclin B (for a review see, Dunphy, 1994, *Trends Cell. Biol.* 4:202–207). Cdc2 kinase activation requires phosphorylation, a process that is regulated by protein phosphatase 2A (for a review, see, Wera & Hennings, 1995, *Biochem. J.* 311:17–29).

It has been discovered that the thyroxine analogues described in copending U.S. Ser. No. 08/655,267 filed Jun. 4, 1996 and U.S. Ser. No. 08/833,272 filed Apr. 3, 1997 exert specific activation of protein phosphatase 2A both in vitro and in vivo. In vivo, activation of protein phosphatase 2A coincides with inhibition of cdc2 kinase and dephosphorylation of MAP kinase and topoisomerase II, rendering both of the latter enzymes inactive. DIME has no metabolic action, nor does it inhibit the biosynthetic pathways of DNA, RNA or proteins. Thus, the most probable mode of action is cell cycle inhibition and induction of apoptosis via dephosphorylation of these critical regulatory proteins. Accordingly, activation of phosphatase 2A and concomitant inhibition of cdc2 kinase is an important and powerful therapeutic target for the treatment of cancer.

While alterations at the ester and 4'-positions appear to significantly affect the effectivity of DIME, thyroxine analogues useful for depressing malignant tumor growth and treating cancer are not limited to DIME. For example, the 4'-ethoxy homologue exhibits about 25–30% maximal cytocidal action on human cancer cells as compared to DIME as is demonstrated in U.S. Ser. No. 08/833,272 filed Apr. 3, 1997. It is also expected that DIME may be substituted at the aromatic ring positions or bridge oxygen without significant loss of activity.

In the general structure for DIME and its homologs and analogs, a methyl ester group is present which is labile with respect to hydrolysis catalyzed by cellular esterases. Since the resultant carboxylic acid from the hydrolysis has much less efficacy against tumor cells than the ester, esterase action imposes a limitation on the efficacy of DIME and its ester homologs. Moreover, amide analogs of DIME, having an $NH_2$ or a substituted amino group, may be subject to hydrolysis catalyzed by cellular amidases. Since the hydrolysis product of such a hydrolysis is a carboxylic acid, the same decrease in efficacy can result. In order to decrease the chemical lability in the DIME pharmacophore structure, ketone analogues of DIME may be used.

Some such ketone structure, for example 1-[3,5-diiodo-4-(4'-methoxyphenoxy)-phenyl]-ethanone (DIPE) has been previously reported in the literature pertaining to the synthesis of thyroxine (R. C. Cookson & G. F. H. Green, J. Chem. Soc. 1952, 827–833; A. Dibbo et al. ibid., 1961, 2890–2902). In that instance, 3,5-diiodo-4-(4'-methoxyphenoxy)cinnamic acid was converted to the ethanone (i.e. methyl ketone).

Using a synthetically more versatile approach, 1-[3,5-diiodo-4-(4'-methoxyphenoxy)-phenyl]-ethanone (DIPE) may be prepared by reacting 3,5-diiodo-4-(4'-methoxyphenoxy)benzoyl chloride (E. T. Borrows et al., J. Chem. Soc. 1949, S185–S190) with dimethylcadmium. In this reaction a methyl group simply displaces the chlorine from the benzoyl chloride. The scope and methodology for preparing ketones by the reaction of organocadmium reagents with acid chlorides has been reviewed by such references as J. Cason "The use of organocadmium reagents for the preparation of ketones", Chem. Rev. 1947, 40, 15–32. Therefore, such ketone analogues of other thyroxine analogues may be routinely prepared by those skilled in the art.

In an analogous manner 1-[3,5-diiodo-4-(4'-methoxyphenoxy)-phenyl]-1-propanone (DIPP) may be synthesized by reacting diethylcadmium with 3,5-diiodo-4-(4'-methoxyphenoxy)benzoyl chloride. Since higher dialkylcadmium and also diarylcadmium species are known to react efficiently with benzoyl chlorides (J. Cason, op. ct.), skilled artisans can make a range of ketones from thyroxine analogues within the scope of the present invention.

It is known that the aromatic rings of thyroxine are not contained within the same plane (Jorgensen, 1978, "Thyroid Hormones and Analogues II. Structure-Activity Relationships," In: *Hormonal Proteins and Peptides*, Vol. VI, pp. 107–204, C. H. Li, ed., Academic Press, New York). It is also known that the ring positions of both of the aromatic rings in thyroxine can be substituted with a variety of substituents, including alkyl, halogen, nitro and amino groups with varying degrees of retention of hormonal activity (ibid). Furthermore, the ether oxygen connecting the rings can be absent or replaced with a variety of groups or atoms that do not confine the aromatic rings to the same plane, such as, for example, a methylene group, a carboxy group or sulfur, without significant loss of hormonal activity (ibid). Accordingly, it is expected and predictable that similar substitutions on DIME will not effect significant loss of anti-cancer activity. Significantly, the 2'-chloro analogue of DIME exhibited about 25% maximal inhibitory action on the growth of human cancer cells as compared to DIME as is demonstrated in copending U.S. Ser. No. 08/833,272 filed on Apr. 3, 1997.

Due to the stringent correlation between in vitro and in vivo efficacy, effective compounds useful in the methods of the invention may be conveniently identified in in vitro assay. Such tests as those shown in copending U.S. Ser. No. 08/655,267 filed Jun. 4, 1996 and U.S. Ser. No. 08/833,272 filed Apr. 3, 1997, herein incorporated by reference, may screen for the ability of a particular compound to activate protein phosphatase 2A. Typically, compounds useful in the methods of the present invention will increase protein phosphatase 2A activity by a factor of about two to three. Such tests may also screen for the ability of a particular compound to inhibit malignant tumor cell growth in vitro or in vivo or abolish tumorigenicity of malignant cells. Generally, active compounds useful in the methods of the present invention will exhibit an $I_{50}$ (concentration of compound lethal to 50% of a cell culture as compared to a control culture) in the range of about 0.5 mm to 5.0 mm, as measured pursuant to the methods described in copending U.S. Ser. No. 08/655,267 filed Jun. 4, 1996 and U.S. Ser. No 08/833,273 filed Apr. 3, 1997.

As will be appreciated by the skilled artisan, many varieties of malignant tumor cell cultures and cell lines may be used to screen for activity, including but not limited to HL-60, HT-144, E-ras-20, DU-145, MDA-168, MCF-7, 855-2 and MDA-MB-231. Of course, other in vitro and/or in vivo assays as will be apparent to the skilled artisan to screen for anti-tumor and/or anti-cancer activity may also be employed to identify effective thyroxine analogues useful in the present invention.

The chemical formulae referred to herein may exhibit the phenomena of tautomerism or conformational isomerism. As the formulae drawings within this specification can only represent one of the possible tautomeric or conformational isomeric forms, it should be understood that the invention encompasses any tautomeric or conformational isomeric forms which exhibit biological or pharmacological activities similar to the specific embodiments, described herein.

In addition to the above-described compounds and their pharmaceutically acceptable salts, the invention may employ, where applicable, solvated as well as unsolvated forms of the compounds (e.g. hydrated forms).

The compounds described herein may be prepared by any process known to be applicable to the preparation of chemical compounds. Suitable processes are illustrated by the representative examples. Necessary starting materials may be obtained by standard procedures of organic chemistry.

Cancers

The ketone thyroxine analogues described herein are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas.

In a preferred embodiment of the invention, the cancer is associated with the formation of solid tumors including, by way of example and not limitation, mammary and prostatic cancers.

Pharmaceutical Formulations And Routes Of Administration

A ketone thyroxine analogue useful in the present invention can be administered to a human patient per se, in the form of a pharmaceutically acceptable salt, or in the form of a pharmaceutical composition where the compound is mixed with suitable carriers or excipient(s) in a therapeutically effective amount, i.e., at doses effective to depress or suppress malignant cell growth or result in amelioration of symptoms associated with cancerous diseases.

Routes Of Administration

The ketone thyroxine analogues and pharmaceutical compositions described herein may be administered by a variety of routes. Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, or intranasal injections.

Alternatively, the compounds may be administered in a local rather than systemic manner, for example via injection of the compound directly into a solid tumor, often in a depot or sustained release formulation. Furthermore, the compounds may be administered in a targeted drug delivery system, for example, in a liposome coated with tumor-specific antibody. The liposomes will be targeted to and taken up selectively by the tumor. In a preferred embodiment, the ketone thyroxine analogues and pharmaceutical compositions described herein are administered orally.

Composition/Formulation

The pharmaceutical compositions described herein may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Other formulations suitable for administering the thyroxine analogues described herein will be apparent to those having skill in the art, and may be found, for example, in *Remington's Pharmaceutical Sciences*, Mack Publishing Co., Easton, Pa., latest edition.

Effective Dosages

Pharmaceutical compositions suitable for use in the present invention include compositions wherein the active ingredients are contained in a therapeutically effective amount. Determination of an effective amount is well within the capability of those skilled in the art, especially in light of the detailed disclosure provided herein. For any compound used in the method of the invention, a therapeutically effective dose can be estimated initially from cell culture assays. For example, a dose can be formulated in animal models to achieve a circulating concentration range that includes the $I_{50}$ as determined in cell culture (i.e., the concentration of test compound that is lethal to 50% of a cell culture) or the $I_{100}$ as determined in cell culture (i.e., the concentration of compound that is lethal to 100% of a cell culture). Such information can be used to more accurately determine useful (loses in humans. $I_{50}$ is 2–10 $\mu$M for most tumors.

Initial dosages can also be formulated by comparing the effectiveness of the thyroxine analogues described herein in cell culture assays with the effectiveness of known anti-cancer drugs such as vincristine. In this method an initial dosage can be obtained by multiplying the ratio of effective concentrations obtained in cell culture assay for the thyroxine analogue and a known anti-cancer drug by the effective dosage of the known anti-cancer drug. For example, if a ketone thyroxine analogue is twice as effective in cell culture assay than vincristine (i.e., the $I_{50}$ is equal to one half times the $I_{50}^{vincristine}$ in the same assay), an initial effective dosage of the ketone thyroxine analogue would be one-half the known dosage for vincristine. Using these initial guidelines one having ordinary skill in the art could determine an effective dosage in humans.

Initial dosages can also be estimated from in vivo data.

Dosage amount and interval may be adjusted individually to provide plasma levels of the active compound which are sufficient to maintain therapeutic effect. Usual patient dosages for oral administration range from about 50–2000 mg/kg/day, commonly from about 250–1000 mg/kg/day, preferably from about 500–700 mg/kg/day and most preferably from about 350–550 mg/kg/day. Preferably, therapeutically effective serum levels will be achieved by administering multiple doses each day. The drug is nontoxic at oral doses of 1 g/Kg/day for two to three months.

In cases of local administration or selective uptake, the effective local concentration of the drug may not be related to plasma concentration. One having skill in the art will be able to optimize therapeutically effective local dosages without undue experimentation.

The amount of composition administered will, of course, be dependent on the subject being treated, on the subject's weight, the severity of the affliction, the manner of administration and the judgment of the prescribing physician.

The chemotherapy may be repeated intermittently while tumors are detectable or even when they are not detectable. Moreover, the therapy may be provided alone or in combination with other anti-cancer or other drugs, such as for example AZT, anti-inflammatories, antibiotics, corticosteroids, vitamins and the like.

Possible synergism between the ketone thyroxine analogues described herein and other drugs is expected and predictable. In addition, possible synergism between a plurality of thyroxine analogues is also expected and predictable.

Toxicity

Toxicity and therapeutic efficacy of the ketone thyroxine analogues described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. It is known that DIME, the parent compound, is not toxic if administered per os at a dose of 1 g/Kg/day for two to three months. The data obtained from these cell culture assays and animal studies can be used in formulating a dosage range that is not toxic for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: *The Pharmacological Basis of Therapeutics*, Ch.1, p.1).

One of the advantages, among others, of using the ketone thyroxine analogues described herein to treat cancer is their lack of toxicity.

The invention having been described, the following examples are offered to illustrate the subject invention by way of example, not by way of limitation.

EXAMPLE 1

Compound syntheses

1-[3,5-diiodo-4-(4'-methoxyphenoxy)-phenyl]-ethanone (DIPE)

In a 10-ml round-bottom flask equipped with a magnetic stirrer and a rubber septum for syringe needles, anhydrous diethyl ether (1.66 ml) and commercial methylmagnesium bromide (Aldrich, 3.0 M solution in diethyl ether) (0.33 ml) were combined and cooled in an ice-bath (15 min). The rubber septum was then temporarily removed and anhydrous cadmium chloride powder (Aldrich) (91.7 mg, 0.50 mmole) was added in portions to the stirred ethereal solution during 2 min. With the rubber septum replaced, the mixture was sequentially stirred at ice-bath temperature (15 min) and with the ice-bath removed (25 min), and then the bulk of the diethyl ether solvent was boiled off by gently heating the flask while using a syringe needle through the septum as a vent to the fume hood. The resultant semi-solid mixture of dimethylcadmium and magnesium halide salts was cooled to ambient temperature and a solution of 3,5-diiodo-4-(4'-methoxyphenoxy)benzoyl chloride (E. T. Borrows et al., J. Chem. Soc. 1949, S185–S190) (0.20 mmole) in benzene (1.50 ml) was added while stirring was maintained for 60 min. The resultant mixture, which is a solution of the product and a suspension of metal halide salts, was then transferred to a small separatory funnel together with ethyl acetate (10 ml) and 0.2 M HCl (aq.) (10 ml). The organic product was extracted into the ethyl acetate, which was then separated from the aqueous phase. After rinsing the ethyl acetate solution with a water wash and drying over anhydrous sodium sulfate, the ethyl acetate and benzene solvents were stripped by rotary evaporation to yield a pale yellow, viscous residue which gradually solidified. The product was isolated from minor impurities by crystallizing it twice from absolute ethanol in the refrigerator (3 C.). Yield: 40.5 mg (40.9%) of off-white crystals. Melting point: 136–138 C. [The literature reports a melting point of 138–143 C. (Dibbo et al. J. Chem. Soc. 1961, 2890–2902)].

Mass spectrum: Low-resolution EI, m/z (relative intensity): 494 ($M^+$, 100), 495 (M+1, 20.8), 479 (22.4), 309 (5.9), 239 (4.5), 225 (7.5). High-resolution data from the $M^+$ peak: calculated for $C_{15}H_{12}O_3I_2$, 493.887598; found, 493.888689 (deviation=−2.2 ppm).

$^1$H NMR spectrum in DMSO-d6 (δ(ppm) values relative to TMS): 2.662 (3H, singlet), 3.775 (3H, singlet), 6.746 (2H, doublet, J=9.16 Hz, plus fine splitting), 6.957 (2H, doublet, J=9.33 Hz, plus fine splitting), 8470 (2H, singlet).

EXAMPLE 2

1-[3,5 diiodo-4-(4'-methoxyphenoxy)-phenyl]-1-propanone (DIPP).

1-[3,5 diiodo-4-(4'-methoxyphenoxy)-phenyl]-1-propanone was prepared exactly analogously to the 1-ethanone structure in the preceding Example, using diethylcadmium instead of dimethylcadmium as reactant with the acid chloride. Diethylcadmium was generated from commercial ethylmagnesium bromide (Aldrich, 3.0 M solution in diethyl ether) (0.33 ml) combined with anhydrous diethyl ether (1.66 ml) and anhydrous cadmium chloride powder (91.7 mg, 0.50 mmole) at ice-bath temperature, using the general methodology detailed in the preceding example. After subsequent stirring at ambient temperature (15 min) and boiling off the bulk of the diethyl ether solvent, the mixture of diethylcadmium and magnesium halide salts was reacted at ambient temperature with a solution of 3,5 diiodo-4-(4'-methoxyphenoxy)benzoyl chloride (E. T. Borrows et al., J. Chem. Soc. 1949, S185–S190) (0.19 mmole) in benzene (1.50 ml) for 60 min. The resultant mixture, which is a solution of product and a suspension of metal halide salts, was worked-up analogously to the preceding example, using ethyl acetate (10 ml) and 0.2 M HCl (aq.) (10 ml). The product was extracted into the ethyl acetate, the solution rinsed with water, then dried over anhydrous sodium sulfate and finally stripped of solvent by rotary evaporation to yield a viscous, pale yellow residue which gradually solidified at ambient temperature. The product was purified by crystallization from absolute ethanol in the refrigerator (3 C.). Yield: 35.3 mg (36.6%) of white crystals. Melting point: 159–162 C. A second crop (8.1 mg., 8.4%) of the product crystals was obtained from the concentrated mother-liquor, but was slightly impure (m.p. 155–159 C.).

Mass spectrum: Low-resolution EI, m/z (relative intensity): 508 ($M^+$, 100), 509 (M+1, 17.9), 479 (47.7), 451 (7.5), 309 (7.5), 239 (10.4). High-resolution data for the $M^+$ peak: calculated for $C_{16}H_{14}O_3I_2$, 507.903248; found, 507.903437 (deviation=−0.4 ppm).

$^1$H NMR spectrum in DMSO-d6 (δ(ppm) values relative to TMS): 1.134 (3H, triplet, J=7.08 Hz), 3.133 (2H, quartet, J=7.17 Hz), 3.777 (3H, singlet), 6.745 (2H, doublet, J=8.92 Hz, plus fine splitting), 6.957 (2H, doublet, J=9.52 Hz, plus fine splitting), 8.472 (2H, singlet).

Other Compounds

Additional ketone thyroxine analogues described herein can be synthesized using the above-described syntheses from appropriate starting materials, as will be readily apparent to those having skill in the art of organic chemistry. Additional guidance can be found in the art, particularly in Borrows et al., 1949, "The Synthesis of Thyroxine and Related Substances. Part I. The Preparation of Tyrosine and Some of its Derivatives, and a New Route to Thyroxine," *J. Chem. Soc.* 1949 (Supp. Issue No. 1):S185–S190; Borrows et al., 1949, "The Synthesis of Thyroxine and Related Substances. Part II. Preparation of Dinitrophenyl Ethers," *J. Chem. Soc.* 1949 (Supp. Issue No. 1):S190–S199; Clayton et al, 1951, "The Synthesis of Thyroxine and Related Substances. Part VIII. The Preparation of Some Halogeno- and Nitro-diphenyl Ethers," *J. Chem. Soc.* 1951: 2467–2473; Gemmill et al., 1956, "3-Iodo-, 3,3'-Diiodo- and 3,3'-Diiodo-5-bromothyroxine," *J. Am. Chem. Soc.* 78:2434–2436; Meltzer et al., 1957, "Thyroxine Analogs," *J. Org. Chem.* 22:1577–1581; Crowder et al., 1958, "Bisbenzylisoquinolines. Part II. The Synthesis of 5-(2-Aminoethyl)-4'-carboxy-2,3-dimethoxydiphenyl Ether," *J. Chem. Soc.* 1958:2142–2149; Jorgensen, 1978, "Thyroid Hormones and Analogues, I. Synthesis, Physical Properties and Theoretical Calculations" In: *Hormonal Proteins and Peptides* Vol. VI, pp. 57–105, C. H. Li, Ed., Academic Press, New York (and references cited therein); and Jorgensen, 1978, "Thyroid Hormones and Analogues, II. Structure-Activity Relationships," In: *Hormonal Proteins and Peptides*, Vol. VI, pp. 107–204, C. H. Li, Ed., Academic Press, New York (and references cited therein).

It has been established that metabolic or metarnorphogenic effects of thyroid hormone analogs depend on their chemical structure. Jorgensen, E. 1978, "Thyroid Hormones and Analogs. II. Structure-Activity Relationships: In Hormonal Protein and Peptides" Vol. VI, Li C H (ed.). Academic Press, New York, pp. 108–203. The hormonally inactive methyl-3,5-diiodo-4-(4'-methoxyphenoxy)benzoate (DIME) was first synthesized in 1949 (Borrows, et al. 1949, "The Synthesis of thyroxine and Related Substances. Part I. The Preparation of Tyrosine and Some of its Derivatives, and a New Route to Thyroxine", *J. Chem. Soc. Suppl. Issue No.* 1:S185–S190) but no significant metabolic or metamorphogenic action of this substance has been reported, Money et al. 1958, "The Effect of Change in Chemical Structure of Some Thyroxine Analogues on the Metamorphosis of Rana pipiens Tadpoles", *Endocrinology* 63:20–28; Stasili et al., 1959, "Antigoitrogenic and Calorigenic Activities of Thyroxine Analogues in Rats", *Endocrinology* 64:62–82; Money et al., 1959, "The Effect of Various Thyroxine Analogues on Suppression of [131]I Uptake by the Rat Thyroid", *Endocrinology* 64:123–125; Kumaoka et al., 1960, "The Effect of Thyroxine Analogues on a Transplantable Mouse Pituitary Tumor", *Endocrinology* 66:32–38; Grinberg et al., 1962, "Studies with Mouse Pituitary Thyrotropic Tumors V. Effect of Various Thyroxine Analogs on Growth and Secretion", *Cancer Res.* 22:835–841. In work commenced earlier by the inventors, DIME has been shown as a potential tumoricidal agent both in cell cultures and in vivo. Kun et al., 1996, "Induction of Tumor Apotosis by methyl-3,5-diiodo-4-(4'-methoxyphenoxy)benzoate (DIME)", Abstract No. 102, *Int. J. Oncol.* 9:supplement 829; Zhen, et al., 1997, "Induction of Metaphase Block and Endoreduplication in Human Cancer Cells by 3,5-diiodo-4 (4'-methoxyphenoxy)benzoate (DIME). Abstract, Amer. Assoc. *Cancer Res.*, Symposium on Cell Signaling and Cancer Treatment, Telfs-Buehen, Austria, Feb. 23–28, 1997. Synthesis and testing of structural homologs and analogs of DIME, differing only in the side chain substitutions, as shown in copending U.S. patent application. Ser. No. 08/655,267, filed Jun. 4, 1996, "Method of Treating Malignant Tumors with Thyroxine Analogs having No Significant Hormonal Activity), delineated the structural specificity for tumoricidal activity of DIME

EXAMPLE 3

Effect on Tubulin Polymerization

In the following experiments the hormonally inactive thyroid hormone analog, DIME, at 1 to 5 mM concentrations inhibits the GTP-dependent polymerization of MTP as determined by an optical test. This inhibition is critically dependent on the concentration of GTP. The quantitative correlation between the concentrations of DIME and GTP, under conditions of a linear rate of MTP polymerization, follows Michaelis-Menten kinetics and the inhibition portrays a "mixed" type, where $k_m$ for GTP and $V_{max}$ are altered simultaneously. Chemical analogues of DIME inhibit MTP polymerization parallel to their antitumorigenic action in vivo. The MTP site is one of the early cellular response sites of DIME.

Exposure of human mammary cancer cells (MDA-MB-231) to 1 mM DIME induced abnormal spindle structures within 18 hours of drug treatment, thus a putative DIME-microtubule-protein (MTP) interaction appears to be a component of early cellular responses to the drug, Zhen, et al., 1997, "Cellular Analysis of the mode of action of methyl-3-5-diiodo-4-(4'-methoxyphenoxy)benzoate (DIME) on tumor cells, *Intl. J. Oncol.* Abnormal spindle structures could be the result of DIME-MTP interaction or reactions of DIME with components of the microtubule organizing center or with as yet undefined systems sequentially or in concert. Since time-dependent quantitative analysis of the MTP system in situ is unsuitable for initial velocity measurement we adapted the in vitro assembly system of neurotubules as a model for a quantitative analysis of the interaction of DIME with MTP. As demonstrated by Gaskin, et al., 1974, "Turbidimetric studies of the in vitro assembly and disassembly of porcine neurotubules", *J. Mol. Biol.* 89:737–758; and Kirschner, et al., 1974, "Microtubules from mammalian brain: some properties of their depolymerization products and a proposed mechanism of assembly and disassembly", *Proc. Natl. Acad. Sci. U.S.A.* 71:1159–1163; this system is suitable for kinetic assay of MTP assembly in vitro. The time course of MTP assembly consists of initiation and propagation and termination steps, Gaskin, et al., 1974, "Turbidimetric studies of the in vitro assembly and disassembly of porcine neurotubules", *J. Mol. Biol.* 89:737–758. The rate of propagation under defined conditions is sufficiently linear to permit kinetic analysis, that can be evaluated with respect DIME and GTP concentrations. As we show here the inhibition of MTP assembly by DIME occurs in the same range of drug concentration as required to inhibit tumorigonesis in vivo, or to inhibit cell replication or induce eventual cell death; Mendeleyev, et al., 1997. "Structural specificity and tumoricidal action of methyl-3, 5-diiodo-4-(4'-methoxyphenoxy)benzoate (DIME)" *Int. J. Oncol.*, 10:689–695. Therefore the DIME-MTP interaction is most probably a component of the apparently pleiotropic cellular mechanism of action of DIME.

Isolation of Microtubule Proteins (MTP)

Preparation of MTP and an optical test for polymerization was adopted from published methods, Gaskin, et al., 1974, "Turbidimetric studies of the in vitro assembly and disassembly of porcine neurotubules", *J. Mol. Biol.* 89:737–758; Tiwari, et al., 1993, "A pH and temperature-dependent cycling method that doubles the yield of microtubule protein", *Anal. Biochem.* 215:96–103. Bovine or rabbit brain was homogenized in an equal volume of ice cold buffer containing 100 mM Pipes/K$^+$ (pH 7.4), 4 mM EGTA. 1 mM MgCl$_2$, 0.5 mM DTT and 0.1 mM PMSF, and centrifuged at 39,000 g for 1 hour at 4° C. To the supernatant, DMSO (8% final concentration) and GTP (1 mM final concentration) were added, followed by incubation at 37° C. for 30 minutes. Microtubules were pelleted at 100,000 g at 37° C. for 30 minutes. The pellets were incubated on ice for 15 minutes, followed by resuspension in ice cold PEM buffer (100 mM Pipes/K+ (pH 6.9), 1 mM EGTA, 1 mM MgCl$_2$). This warm polymerization and cold depolymerization cycle was repeated once more and the cold, resuspended monomeric MTP (8–10 mg/ml protein) was used for the optical test for polymerization kinetics. Both rabbit or bovine brain yielded identical MTP preparations.

The polymerization reaction was started by the addition of 100 ml of MTP solution (equivalent to 0.8–1.0 mg protein) and initial linear rates of increase in absorbance at 350 nm followed and recorded at 37° C. in a Perkin-Elmer 552 double beam spectrophotometer, equipped with a thermostatically controlled cuvette holder.

Results and Discussion

It is apparent that the rate of MTP polymerization proceeds in a linear manner, thus conditions for maximal polymerization rates as defined by Berne, B, 1974, "Interpretation of light scattering from long rods", *J. Mol. Biol.* 89:755–758 appear fulfilled. Therefore it is possible to determine the quantitative correlation between [DIME] and [GTP] by comparing the linear rate in the presence of varying drug and activator concentrations. At 1 mM GTP concentration, increasing concentrations of DIME progressively inhibit MTP polymerization.

Inhibition of 1 mM DIME quantitatively correlated with [GTP] and a double reciprocal plot produced a "mixed" type inhibition, Dixon, et al., 1964 *Enzymes*, pp. 234–237, Acad. Press, Inc., New York. Both $V_{max}$ and $k_m$ values were changed by nearly 50% $k_m$ GTP from 6.7 mM to 14 mM, while $V_{max}$ decreased by close to 50%. The simplest interpretation of a mixed inhibition, based on the Briggs-Haldane equation (cf. 7) is that $k_2$, i.e., the dissociation [ES] to E and P (product), is directly affected which then modifies both $k_m$ and $V_{max}$. The exact nature of $k_2$ is presently unknown and its determination requires analysis of reaction products of GTP hydrolysis, a work to be reported elsewhere. Allosteric modifications may also accomplish similar results, Dixon, et al., 1964 *Enzymes*, pp. 234–237, Acad. Press, Inc., New York. The purpose of the present experiments is to compare the effectivity of DIME with some of its analogues on MTP polymerization and correlate results with cytophathologic processes (e.g., inhibition of tumorigenesis in vivo).

There is apparent correlation between the chemical structure of DIME and 7 of its analogues that act on MTP polymerization and their inhibitory potency on in vivo tumorigenesis (compare with Table 1 and Mendeleyev et al supra). For example substitution $R_1$ from $CH_3O$ to EtO and n-BuO progressively diminishes inhibition of MTP polymerization, almost exactly parallel to the decreasing antitumorigenic effect. On the other hand, substitution in $R_2$ from the methyl ester to the carboxylic acid completely abolishes the inhibitory effect on MTP polymerization but only halves the antitumorigenic action, tested with E-ras 20 cells. It is possible that such quantitative differences may reflect cell type specific variations.

TABLE 1

Effect of DIME and some analogs on microtubule assembly in vitro

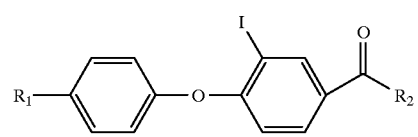

| Compound No. | $R_1$ | $R_2$ | Percent inhibition of intitial velocity |
|---|---|---|---|
| 1 | $CH_3O$ | $CH_3O$ | 93 |
| 2 | EtO | $CH_3O$ | 76 |
| 4 | n-BuO | $CH_3O$ | 8 |
| 6 | $CH_3O$ | HO | 0 |
| 5 | $CH_3O$ | EtO | 35 |
| 7 | $CH_3O$ | $H_2N$ | 43 |
| 9 | $CH_3O$ | $(CH_3)_2N$ | 6 |
| 18 | $CH_3O$ | $CH_3O$ | 7 |

The assay system consisted of 240 μl of PEM buffer containing 8% DMSO and GTP (final concentration 1 mM), 10 μM final concentration of drug (added in 3 μl), or solvent control and 0.6 mg MTP (60 μl). Microtubule assembly at 37° C. was monitored at λ = 350 nm and initial velocities were calculated as $mA_{350}$/min. The control had an initial velocity of 180 $mA_{350}$/min. The values are averages of duplicate assay.

Inhibition of MTP polymerization may have highly complex cellular consequences. In cytokinesis this inhibition may interfere with traction forces of tubulin and prevent the formation of a cleavage furrow which is essential for cell division, Burton, et al., 1997, "Traction forces of cytokinesis measured with optically modified elastic substrate", *Nature* 385:450–454. The inhibition of MTP polymerization by DIME should be correlated with the biochemical sites of this drug. As compared with Mendeleyev et al; supra, DIME directly activates protein phosphatase 2A, therefore it is necessary to coordinate this effect with mitosis-related phenomena induced by DIME. For example it was recently reported, Kawabe, et al., 1997, "HOXII interacts with protein phosphatase 2A and pp1 and disrupts G2/M cell cycle check point" *Nature* 385:454–458. Protein phosphatase 2A may regulate G2/M transition and pp2-A is also a potential oncogene, the inhibition of which promotes oncogenesis. It is possible that activation of pp2A by DIME be aantagonistic to oncogenesis.

On the basis of these experiments, it can be seen that thyroxine type analogues, such as DIME, are capable of blocking mitosis in cancer cells.

EXAMPLE 4

Molecular Pharmacological Properties of DIPE and DIPP, and Comparison with DIME.

The effects of these three substances on the growth of human mammary cancer cells (MDA-MB-231) and human lung cancer cells (A 549) are summarized in Table 2.

In section (a) of Table 2 the effects of DIME, DIPE and DIPP on the growth of mammary cancer cells, assayed at 48 and 72 hrs, is shown. At 2 μM all three drugs had a similar growth depressant effect, except at 72 hrs. DIPP was about one half as effective as the other two drugs. The slightly lesser efficacy of DIPP could be predicted from earlier results obtained with DIME analogs (International Journal of Oncology, 1997, 10, 689–695, FIG. 1) where we have shown that extending the methyl to ethyl substitution (on the carboxyl ester) diminishes cytotoxicity against tumor cells. A similar phenomenon occurs when DIPE is extended to DIPP (i.e. from the ethanone to the propanone).

In Table 2 (b) the cytocidal action of DIPE (2 μM) on lung cancer cells is shown, and it is apparent that the esterase inhibitor (bis[4-nitrophenyl]phosphate, BNPP) had no supportive effect, consistent with the absence of esterase action on DIPE.

In Table 2(c) the effect of DIME is illustrated (on lung cancer cells) and here the esterase inhibitor supported the DIME effect (at 72 hrs), consistent with elimination, by the esterase inhibitor, of hydrolytic inactivation of DIME.

The effect of DIME and DIPE on colony formation by mammary cancer cells is illustrated in FIG. 1, where the results are superimposable, confirming that cytocidal action of DIME and DIPE are indistinguishable.

Figure 2:
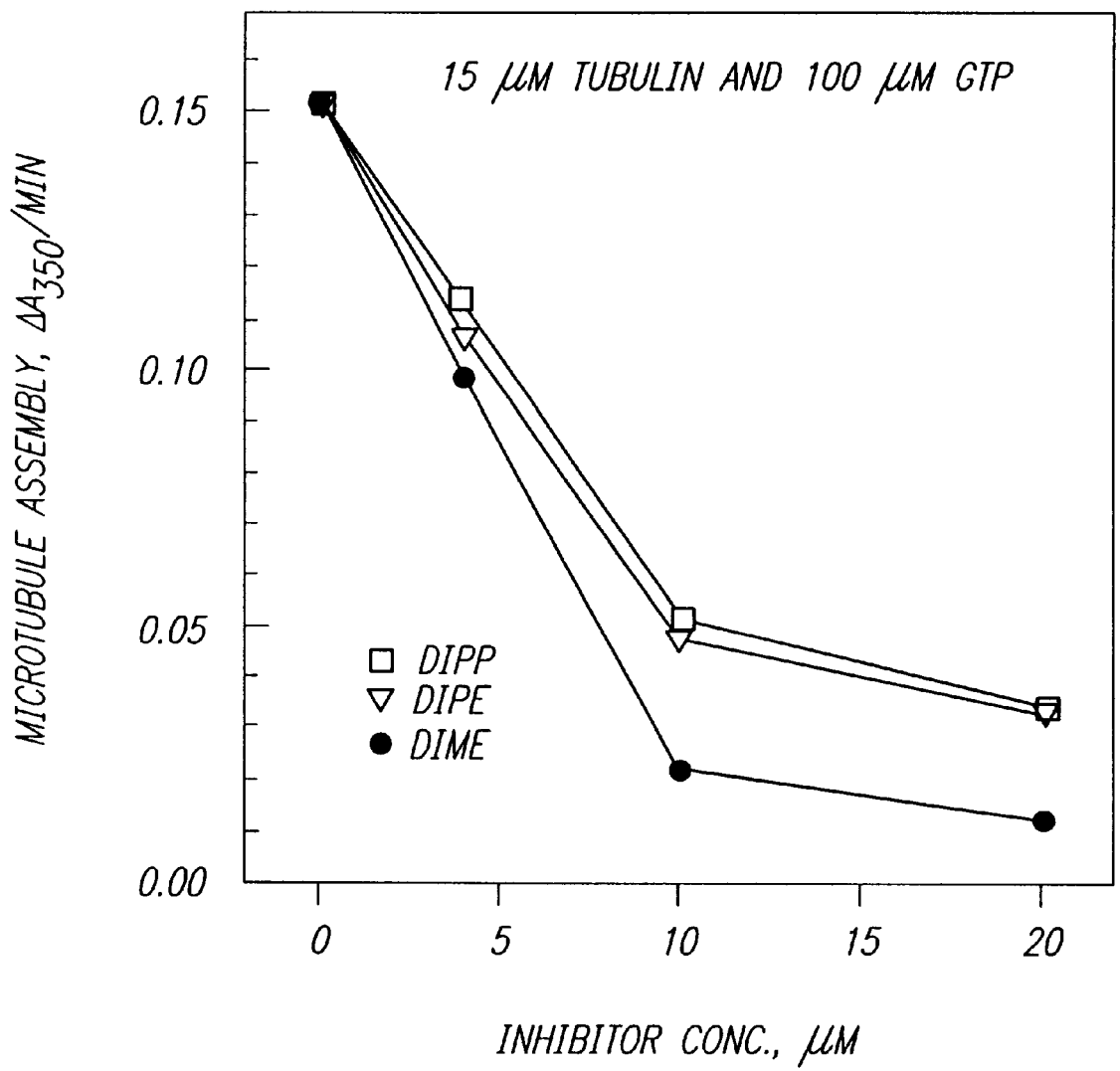
FIG. 2 is a graph illustrating the inhibitory action on microtubule assembly of methyl 3,5-diiodo-4-(4'-methoxyphenoxy)benzoate (DIME), 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP) at drug concentrations ranging up to 20 $\mu$M.

We have reported that one of the characteristic molecular modes of action of DIME consists of inhibition of microtubule protein (MTP) assembly (Buki, et al., International Journal of Oncology 1997, 10, 911–913). Therefore we also compared the effects of DIME, DIPE and DIPP at a concentration range up to 20 $\mu$M on MTP assembly as shown in FIG. 2. The action of all three drugs is similar, thus providing evidence that replacements of the methyl ester structure in DIME does not fundamentally alter the antitubulin assembly effects.

Figure 3:
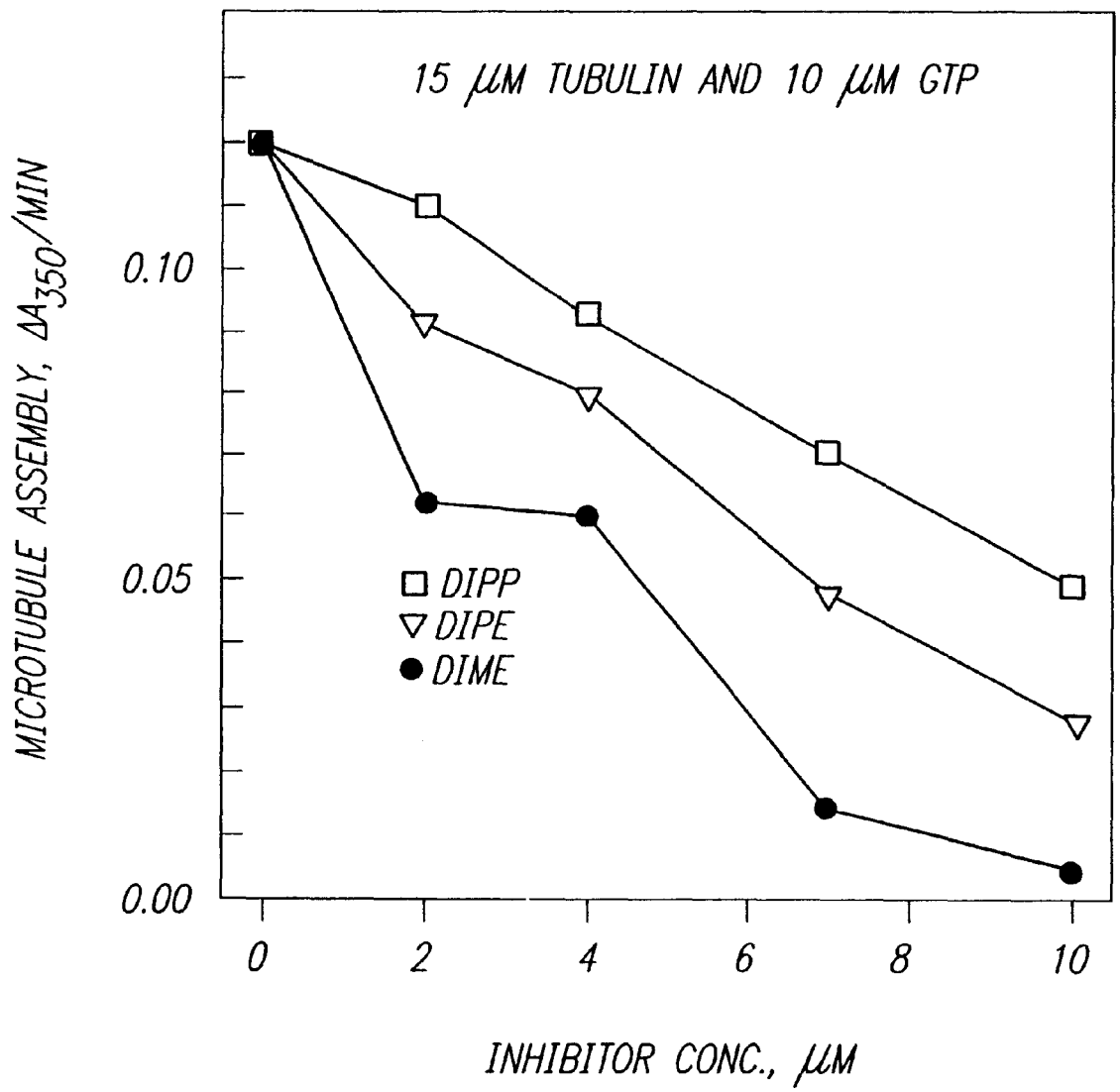
FIG. 3 shows the inhibitory action on microtubule assembled of methyl 3,5-diiodo-4-(4'-methoxyphenoxy)benzoate (DIME), 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP) at lowered GTP concentration (10 $\mu$M).

A more detailed kinetic comparison of DIME, DIPE and DIPP on the kinetics of MTP assembly, in a concentration range of zero to 10 $\mu$M drug and a louvered GTP concentration (10 $\mu$M), is shown in FIG. 3. It is evident that the potency of MTP assembly is DIME>DIPE>DIPP, similar to the results obtained by assaying cylocidal action (FIG. 1), supporting the conclusion that esterase-insensitive DIME analogs act very similar to DIME, but possess the advantage of biochemical stability against esterase action.

TABLE 2

Comparison of the Effects on Cancer Cell Growth of Compounds DIME, DIPE, and DIPP

| | Hours of Incubation | |
|---|---|---|
| | 48 | 72 |
| | ($\times 10^3$) Cell number per 2 $cm^2$ well | |
| (A) MDA 23 1 (breast cancer cells) | | |
| Control (no addition) | 150 | 300 |
| DIME 2 $\mu$M | 60 | 65 |
| DIPE 2 $\mu$M | 55 | 60 |
| DIPP 2 $\mu$M | 90 | 145 |
| (B) A549 (lung cancer cells) | | |
| Control | 110 | 190 |
| DIPE 2 $\mu$M | 78 | 81 |
| DIPE 5 $\mu$M | 38 | 40 |
| DIPE 5 $\mu$M + BNPP 150 $\mu$M | 37 | 38 |
| DIME 2 $\mu$M | 100 | 180 |
| DIME 5 $\mu$M | 72 | 135 |
| DIME 5 $\mu$M + BNPP 150 $\mu$M | 24 | 15 |

The written description enables one skilled in the art to practice the invention. Various modifications of the above-described modes for carrying out the invention which are obvious to those skilled in the pharmaceutical arts or related fields are intended to be within the scope of the claims.

What is claimed is:

1. A method of treating a malignant tumor sensitive to the compounds below, in a mammal, the method comprising administering to said mammal an effective amount of a ketone thyroxine analogue having no significant hormonal activity, in an amount sufficient to depress growth of the malignant tumor, wherein the ketone thyroxine analogue is characterized as being a comnpound capable of inhibiting initial velocity of microtubule protein assembly in vitro wherein said thyroxine analoaue has the formula:

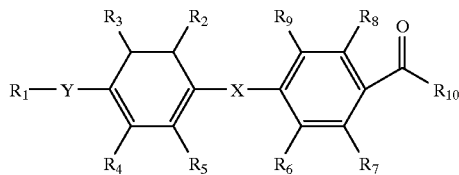

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen;
$R_6$, $R_7$, $R_8$ and $R_9$ are independently selected from the groups consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$; and
$R_{10}$ is selected from the group consisting of ($C_1$–$C_4$) alkyl, ($C_1$–$C_4$) alkenyl, and ($C_1$–$C_4$) alkynyl.

2. The method according to claim 1, wherein the ketone thyroxine analogue has the formula:

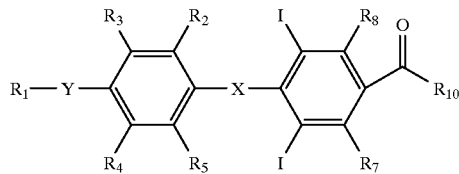

and pharmaceutically acceptable salts thereof, wherein:
X=O, S, $CH_2$, carboxy or absent;
Y=O or S;
$R_1$=methyl or ethyl;
$R_2$, $R_3$, $R_4$ and $R_5$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy and halogen;
$R_7$ and $R_8$ are independently selected from the group consisting of: H, ($C_1$–$C_4$) alkyl, ($C_1$–$C_4$) alkenyl, ($C_1$–$C_4$) alkynyl, hydroxyl, ($C_1$–$C_4$) alkoxy, halogen, $NO_2$ and $NH_2$; and
$R_{10}$ is selected from the group consisting of ($C_1$–$C_4$) alkyl, ($C_1$–$C_4$) alkenyl, and ($C_1$–$C_4$) alkynyl.

3. The method according to claim 1, wherein the ketone thyroxine analogue is selected from the group consisting of 1-[3,5-diiodo-4-(4'-methoxyphenoxy)-phenyl]-ethanone (DIPE) and 1-[3,5-diiodo-4-(4'-methoxyphenoxy)-phenyl]-1-propanone (DIPP).

4. The method according to claim 1, wherein the ketone thyroxine analogue is administered in an amount effective to cause regression of the malignant tumor.

5. The method according to claim 1, wherein the malignant tumor is selected from the group consisting of carcinoma and sarcoma.

6. The method according to claim 1 wherein the ketone thyroxine analogue is administered orally.

7. A method of treating cancer sensitive to the compounds below, the method comprising administering to a mammal having cancer an amount of a ketone thyroxine analogue effective to treat cancer, wherein the ketone thyroxine analogue has the structural formula:

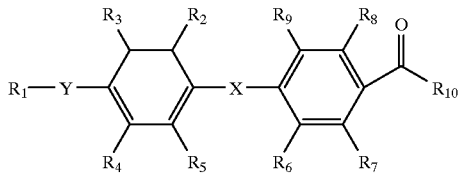

and pharmaceutically acceptable salts thereof, wherein:

X=O, S, $CH_2$, carboxy or absent;

Y=O or S;

$R_1$=methyl or ethyl;

$R_2$, $R_3$, $R_4$ and $R_5$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy and halogen;

$R_6$, $R_7$, $R_8$ and $R_9$ are independently selected from the group consisting of: H, $(C_1-C_4)$ alkyl, $(C_1-C_4)$ alkenyl, $(C_1-C_4)$ alkynyl, hydroxyl, $(C_1-C_4)$ alkoxy, halogen, $NO_2$ and $NH_2$; and $R_{10}$ is selected from the group consisting of $(C_1-C_4)$ alkyl, $(C_1-C_4)$ alkenyl and $(C_1-C_4)$ alkynyl.

* * * * *